United States Patent
Hunt et al.

(10) Patent No.: US 6,300,633 B1
(45) Date of Patent: Oct. 9, 2001

(54) IN-LINE METHOD FOR DETERMINING THE RESIDUE CONTENT OF AN ISOCYANATE AND APPARATUS USEFUL THEREFOR

(75) Inventors: Robert N. Hunt, Steubenville, OH (US); Gary F. Allen, New Martinsville, WV (US); Julie A. Jackson, Houston; Peter Scharein, Baytown, both of TX (US); Peter J. Ryan, Leverkusen (DE); Donald Macnaughton, Jr., New Martinsville, WV (US); Klaus Sommer, Pittsburgh, PA (US); Larry E. Philyaw, Seabrook, TX (US)

(73) Assignee: Bayer Corporation, Pittsburgh, PA (US)

(*) Notice: Subject to any disclaimer, the term of this patent is extended or adjusted under 35 U.S.C. 154(b) by 0 days.

(21) Appl. No.: 09/110,526

(22) Filed: Jul. 6, 1998

(51) Int. Cl.[7] ....................................................... G01J 5/02
(52) U.S. Cl. ......................... 250/339.12; 526/69; 526/70; 528/70
(58) Field of Search ........................ 250/339.12; 526/59, 526/60; 528/70

(56) References Cited

U.S. PATENT DOCUMENTS

| | | |
|---|---|---|
| 4,771,629 | 9/1988 | Carlson et al. . |
| 4,910,403 | 3/1990 | Kilham et al. . |
| 5,151,474 * | 9/1992 | Lange et al. . |
| 5,153,140 * | 10/1992 | Langefeld et al. . |
| 5,206,701 * | 4/1993 | Taylor et al. . |
| 5,223,715 * | 6/1993 | Taylor . |
| 5,287,168 | 2/1994 | Poucher et al. . |
| 5,521,384 | 5/1996 | Lynch . |
| 5,532,487 | 7/1996 | Brearley et al. . |

FOREIGN PATENT DOCUMENTS

98/23296  6/1998 (WO) .

OTHER PUBLICATIONS

Dumoulin M M et al: "Techniques for Real–time Monitoring of Polymer Processing", Trends in Polymer Science, vol. 4, No. 4, Apr. 1, 1996, pp. 109–114, XP004049245 ISSN: 0966–4793, p. 112.

* cited by examiner

Primary Examiner—Constantine Hannaher
Assistant Examiner—Andrew Israel
(74) Attorney, Agent, or Firm—Joseph C. Gil; Lyndanne M. Whalen; Carolyn M. Sloane

(57) ABSTRACT

An in-line spectrometric method for determining the distillation residue content in an opaque, dark-colored mixture containing an isocyanate and tar-like materials (residue) during the isocyanate production process. A probe capable of directing light at wavelengths of from 1050 to 2150 nm is inserted in a stream of the residue-containing mixture and light is transmitted through the stream. Light absorption data is collected and a near-infrared spectrum is generated. The residue content is then determined using a chemometric model. Knowledge of the residue content makes it possible to control and optimize the distillation process.

11 Claims, 6 Drawing Sheets

US 6,300,633 B1

IN-LINE METHOD FOR DETERMINING THE RESIDUE CONTENT OF AN ISOCYANATE AND APPARATUS USEFUL THEREFOR

BACKGROUND OF THE INVENTION

The present invention relates to (1) an in-line spectrometric method for determining the distillation residue content in an opaque, dark-colored mixture containing an isocyanate and tar-like materials (hereinafter referred to as an "isocyanate/residue mixture") during the isocyanate production process, (2) the use of the residue content information to control and optimize the distillation process and (3) an apparatus useful for making such residue content determination.

The use of spectral analysis to determine the identity and physical properties of materials is known. Processes in which materials are analyzed during production (i.e., an in-line process) rather than a few hours or days later have long been sought. The advantages of an in-line process are obvious. In-line analysis would eliminate the long turn-around time experienced with traditional lab analysis and would make it possible to optimize the production process by identifying deviations or necessary corrections within a substantially shorter period of time than that which is possible when traditional analytical quality control methods are used.

U.S. Pat. No. 5,151,474 discloses a process control method for a polyolefin polymerization process. In this disclosed process, monomer and co-monomer are added to a flowing stream of solvent at a constant rate. The concentration of monomer and co-monomer in the solvent stream are determined by high resolution multi-wavelength vibrational spectroscopic analysis (e.g., Fourier transform infrared spectroscopy). The rate of addition of the monomer and/or co-monomer is adjusted as needed on the basis of this spectroscopic analysis. Such addition rate adjustments during the production process reduce the variation in product density.

U.S. Pat. No. 5,153,140 discloses a process for controlling and optimizing industrial processes for the production of dyes, fluorescent whitening agents and their intermediates. In this process, differential analysis of the UV/VIS absorption spectra of at least one starting compound and at least one reaction product are used to monitor and control the production process.

U.S. Pat. Nos. 5,206,701 and 5,223,715 disclose specially designed spectrophotometric apparatus for quantifying the physical properties of hydrocarbons, crude petroleum and other black oils. In these specially designed apparatus, a sample cell or probe may be inserted directly into the sample source. The spectral data generated are related to the physical properties of the product by means of chemometric models.

These prior art processes do not, however, disclose a method for process control in which the concentration of tar-like by-products generated during the production process in the distillation residue may be monitored using standard, commercially available equipment. Monitoring the residue by-product content rather than amount of reactant material(s) or reaction product is advantageous because product loss is minimized and formation of a large concentration of residue that could cause processing problems is avoided. However, because the residue of a distillation process is generally opaque and dark in color and more varied in composition than the desired product or the reactants, it is more difficult to monitor such residue by an in-line process.

An in-line spectrometric process for monitoring a residue that generates the desired analyses with a high degree of accuracy within a very short period of time using standard, commercially available equipment would therefore be advantageous.

SUMMARY OF THE INVENTION

It is an object of the present invention to provide an in-line spectrometric method for determining the residue content of an isocyanate production distillation residue containing tar-like by-products within an accuracy of ±2.0%.

It is also an object of the present invention to provide an in-line method for determining residue content which may be carried out using standard, commercially available equipment.

These and other objects which will be apparent to those skilled in the art are accomplished by positioning a near infrared (NIR) probe in the isocyanate distillation vessel or a pipeline through which isocyanate/residue mixture is transported in a manner such that the isocyanate/residue mixture will pass or flow through the sample cell of the probe. The NIR probe which is used must be capable of (1) transmitting light from an NIR source at wavelengths of from 1050 to 2150 nanometers (nm) through an isocyanate/residue mixture and (2) relaying that transmitted light over fiber optic cables which connect the probe to the NIR source and to an NIR spectrometer. The NIR spectrometer must be capable of generating an NIR second derivative absorption spectrum from the light which has been transmitted through the isocyanate/residue mixture to the spectrometer via fiber optic cable. The residue content of the isocyanate/residue mixture is determined from the second derivative spectrum using a mathematical (chemometric) model.

DETAILED DESCRIPTION OF THE PRESENT INVENTION

Figure 1:
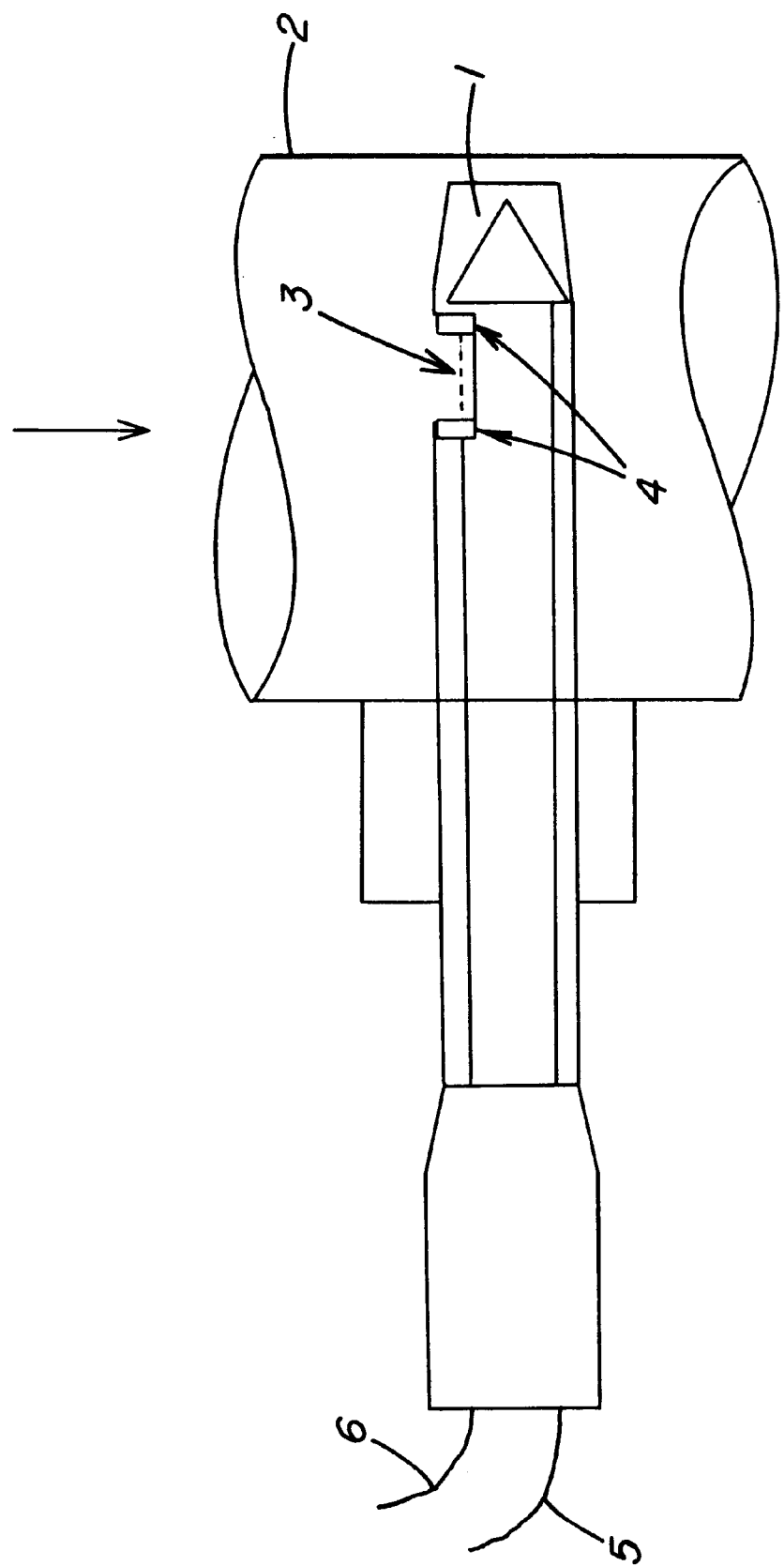
FIG. 1 is a diagram of an in-line NIR probe that is capable of transmitting light through a sample cell portion of the probe containing a mixture of isocyanate and residue containing tar-like by-products as the isocyanate/residue stream flows through a pipeline.

The present invention relates to an in-line spectrometric method for determining the distillation residue content and optionally other characteristics of an isocyanate/residue mixture during the isocyanate production process. This invention also relates to a method in which the residue content information is used to control and optimize the distillation process by which product isocyanate is recovered. The invention further relates to an apparatus suitable for us in the spectrometric method for determining distillation residue content.

Diisocyanate 5 and polyisocyanates are generally produced by phosgenating an organic amine. The desired diisocyanate or polyisocyanate is recovered from the phosgenated mixture by distillation. As isocyanate is distilled off from the phosgenated mixture, a residue is generated. This residue includes not only unrecovered isocyanate but also by-products which are dark and tar-like. It would, of course, be advantageous to reduce or eliminate the formation of these unwanted by-products as the desired isocyanate product is recovered. However, in order to achieve such reduction, it is necessary to adjust the distillation temperature and absolute pressure conditions as the relative amount of desired product remaining in the distillation vessel decreases.

The present invention makes it possible to determine the relative amount of residue present during the distillation process by which the desired product is recovered. This determination makes it possible to better control the distillation process and to optimize isocyanate product recovery.

As used herein, "residue content" means the relative amount of unwanted by-products present in a mixture of product isocyanate and unwanted by-products. Residue content is expressed in terms of % by weight residue, based on the total weight of isocyanate/residue mixture.

The residue content and any other properties or characteristics of the isocyanate/residue mixture which are measured in accordance with the present invention (e.g., density, viscosity) are determined by means of a mathematical (chemometric) model developed for the specific isocyanate and its residue. More specifically, NIR spectra which have been generated from an isocyanate/residue mixture being evaluated is compared with "reference" spectra that have been correlated with residue content (or some other property or characteristic of a residue) to generate a model. Comparison of the NIR spectra of the residue being evaluated with the model for that type of residue will generally be carried out by means of a computer which has been programmed with the model correlating the absorption of radiation at selected wavelengths with the residue content and/or selected property. Generally, this computer is connected to and interfaces with the NIR spectrometer to generate an output that is interfaced with the main isocyanate production process control computer. The output may be displayed on a monitor connected to the main isocyanate production process control computer. The production operating personnel can use the residue content information to control the isocyanate recovery process by adjusting the processing conditions (e.g., temperatures of the distillation columns and/or absolute pressure of the distillation column (s)). The residue content output may also be used to control the process temperatures and absolute pressure in a closed loop by the main production process control computer.

Figure 2:
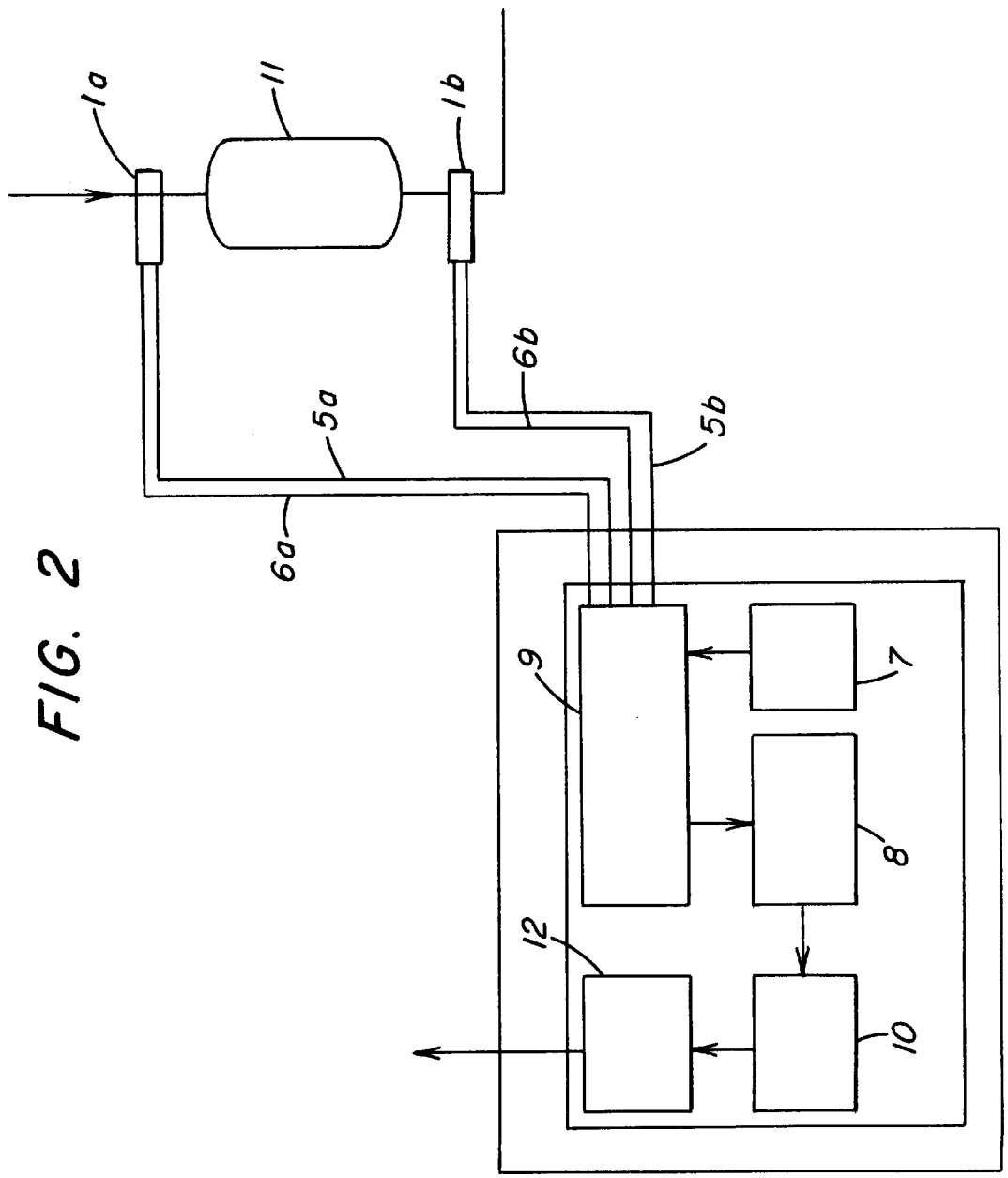
FIG. 2 is a schematic representation of an apparatus within the scope of the present invention in which the remote location of the NIR probe illustrated in FIG. 1 with respect to the NIR spectrometer and isocyanate distillation vessel is demonstrated.
Figure 3:
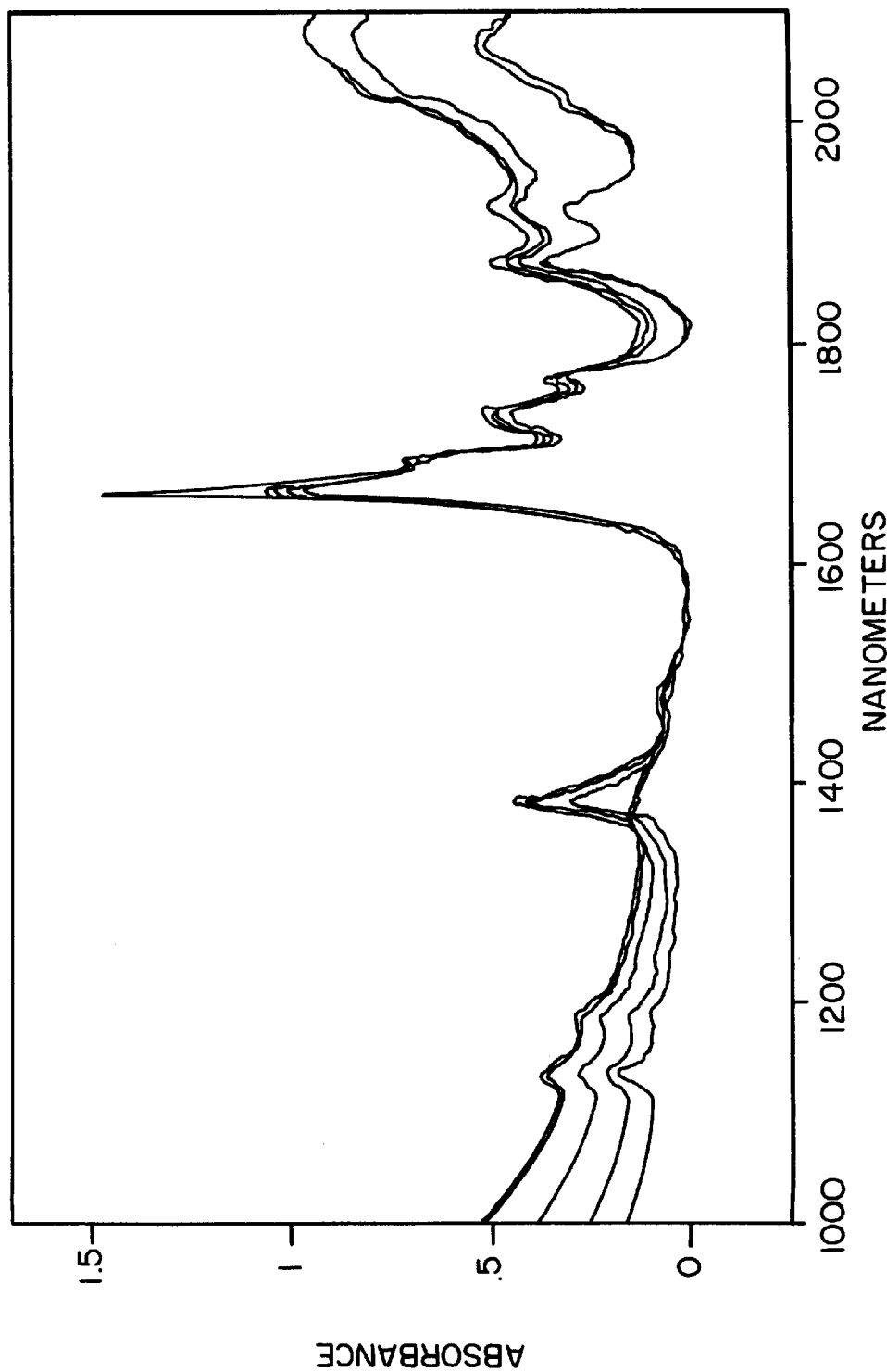
FIG. 3 is a plot of the generated absorption spectra of a toluene diisocyanate residue mixture having a residue content varying from 11 to 48 percent.

The method and apparatus of the present invention may be better understood when explained in reference to FIGS. 1 and 2.

As shown in FIG. 1, probe 1 is inserted directly into a stream of isocyanate containing residue as it flows through pipeline 2. Sample cell 3 is positioned on probe 1 between two NIR windows 4. Optical fiber 5 connects probe 1 with a remote NIR source 7 (shown in FIG. 2). Optical fiber 6 connects probe 1 with a remote spectrometer 8 (shown in FIG. 2).

As shown in FIG. 2, probe 1a is positioned in an isocyanate/residue stream at a point before that isocyanate/residue stream enters distillation column 11. Probe 1b is positioned in the isocyanate/residue stream at a point after the isocyanate/residue stream has passed through distillation column 11. NIR light is transmitted via optical fiber 5a to probe Ia and via optical fiber 5b to probe 1b from NIR source 7. This light passes through the isocyanate/residue mixture as it flows between the NIR windows of the sample cells (shown in FIG. 1) of the probes to multiplexer 9 and then to spectrometer 8. The spectra generated by spectrometer 8 are then relayed to computer 10 where the data is analyzed using the appropriate chemometric model. The results of this analysis are then relayed to monitor 12 where they are shown on a screen.

The beam of light used to generate the NIR spectra is transmitted from an NIR source capable of emitting light at wavelengths of from 1000 to 2100 nm, preferably from 1715 nm to 1973 nm. Any NIR source with a strong emission in the 1000 to 2100 nm range may be used to practice the method of the present invention. An example of a suitable NIR source is a UOP Guided Wave Tungsten Source, part number P/N 17925-001 which is available from UOP Guided Wave Process Analytical Systems of El Dorado Hills, Calif.

Any optical fiber or cable which is capable of relaying the NIR beam from the NIR source to the probe without absorbing any significant amount of the optical energy in the beam may be used in the practice of the present invention. Suitable fiber or cable will generally have a diameter of from about 300 $\mu$m to about 1000 $\mu$m, preferably about 500 $\mu$m. This fiber or cable should be capable of transmitting light without distortion within wavelength ranges of from about 1000 nm to about 2100 nm, preferably from about 1500 nm to 2000 nm. A specific example of suitable commercially available fiber or cable is the UOP Guided Wave VIS-NIR Jacketed Optical Fiber part number P/N 12538-100 that is 500 $\mu$m fiber terminated in SMA 905 connectors with a spectral transmission range of 400 to 2100 nm which is available from UOP Guided Wave Process Analytical Systems of El Dorado Hills, Calif.

The NIR probe is positioned in or mounted on either (1) a vessel containing a mixture of isocyanate and residue (process stream) from an isocyanate production process or (2) a pipeline through which such mixture is being transported. The probe is positioned so that: (1) it will be exposed sufficiently to the contents of the vessel or pipeline, and (2) the contents of the vessel or pipeline flow freely through the sample cell portion of the probe without restriction. In order to maximize optical throughput of the NIR beam and to maintain sufficient response to the residue absorption peaks, it is preferred that the probe sample cell be approximately 1 centimeter long.

Any of the known and commercially available NIR probes which is capable of functioning at the temperatures and pressures present in the residue-containing vessel or pipeline (i.e., temperatures of from about 24 to about 200° C. and pressures of from −14.7 psig to about 600 psig) may be used. A specific example of a suitable commercially available probe is the UOP Guided Wave Single-Sided Transmission (SST) Probe with a 1 cm sample cell path length which is available from UOP Guided Wave Process Analytical Systems of El Dorado Hills, Calif.

The NIR beam interfaces with the process stream by exiting the probe body through the first probe NIR window of the sample cell, passing through the process stream as that stream passes through the sample cell of the probe and reentering the probe body at the second probe NIR window of the sample cell. The NIR beam is attenuated as a function of the composition of the process stream. The NIR windows and sample cell are an integral part of the NIR probe. Any window material that transmits in the 1000 to 2100 nm spectral region and functions at the temperatures and pressures to which the NIR probe will be subjected during the isocyanate production and recovery processes is suitable. The preferred window material is sapphire.

The NIR beam is transmitted from the NIR probe to the NIR spectrometer over a second optical fiber having characteristic properties comparable to or identical to those of the first optical fiber (i.e., the fiber connecting the probe to the NIR source).

The spectrometer measures the absorption spectrum of the process stream. Any of the commercially available near infrared ("NIR") spectrometers may be used in the practice of the present invention. Such spectrometers are capable of generating spectra from absorbed light having wavelengths of from about 1000 to about 2100 nm, preferably from about 1500 to about 2000. A specific example of a suitable commercially available NIR spectrometer is the Guided Wave Model 310 having an operating spectral region of from 1050 to 2000 nm which is available from UOP Guided Wave Process Analytical Systems of El Dorado Hills, Calif.

The NIR spectrometer is located at a position which is remote from the isocyanate/residue stream being tested and the test probe. The NIR spectrometer is connected to a device or devices capable of controlling it, correlating data from the spectrometer with a pre-programmed model specific to the particular isocyanate and residue being monitored, and outputting the calculated % residue concentration to an external device for display or control using a 4–20 milliampere (ma) loop controller.

Connection between the NIR spectrometer and control device (e.g., computer) is generally by wire cable capable of transmitting data between the spectrometer and the control device. The preferred cable is a RS-232 cable connected to the serial data ports between the spectrometer and control device.

The device which controls the spectrometer and correlates data is generally a computer. Any of the commercially available computers having the capacity or ability to collect and correlate data in the manner required by the method of the present invention may be used. Examples of suitable computers include: an IBM compatible 486 66 mHz based computer running Microsoft DOS 6.0 or higher and a Gateway 2000 Model 4DX2-66V (particularly preferred).

The device for controlling the 4–20 ma loop to external devices is generally an interface board installed in the computer. A suitable 4–20 ma interface board which is commercially available is a Model # CIO-DAC02 2 channel, 12 Bit D/A plug in card available from Omega Engineering, Inc.

The external device for display and/or control is any such device which can accept a 4–20 ma loop input. The control device may be the process control computer for the isocyanate production unit. The preferred process control computer is a Fisher Provox computer which is commercially available from Fisher. The display device may be any monitor connected to the control device.

The control device (computer) connected to the spectrometer should generally be programmed with software capable of controlling the actions of the spectrometer system and gathering and processing the data from said spectrometer. Any of the commercially available programs having this capability may be used. A specific example of a suitable commercially available program is the UOP Guided Wave Model 300 System Software for real time spectrometer control, data collection, and analysis which is available from UOP Guided Wave Process Analytical Systems of El Dorado Hills, Calif.

Processing to be done by the control device (e.g., a computer) includes: (1) collecting raw transmission spectrum data files from the spectrometer; (2) generating an absorption file by taking the log to the base ten of the ratio of the raw transmission spectrum to a stored reference transmission spectrum; (3) generating second derivative absorption spectra; (4) generating the % residue in the isocyanate plus residue mixture being analyzed from the product sum of the second derivative absorption spectrum with the coefficient file of the pre-programmed model; and (5) selecting the % residue concentration to be relayed to the 4–20 ma interface board.

The composition of the residue from the isocyanate production process which is being analyzed will, of course, be dependent upon the particular isocyanate being produced and the specific processing conditions. It is therefore necessary to calibrate or build a chemometric model for each isocyanate and production unit. The correlation between the near infrared spectrum of the isocyanate and residue mixture may be established for toluene diisocyanate, for example, by determining the residue content in a toluene diisocyanate/residue mixture using traditional analytical techniques. This residue content information is then correlated with the corresponding NIR spectrum to build a model for percent residue. More specifically, the mathematical model was developed from spectral and residue content data obtained on multiple representative samples of the isocyanate and residue mixtures collected during actual isocyanate production. Near infrared spectral data were obtained for each of these samples. The residue content of each sample was determined in the laboratory by thermogravimetric analysis. A specific example of a suitable commercially available thermogravimetric apparatus for making said residue determinations is the Mettler M3 Balance with the Mettler TC 15 TA controller which is available from Mettler.

The mathematical (chemometric) model for the isocyanate and residue being analyzed may be developed for properties such as percent residue content using any software capable of multivariate regression analysis. Pirouette Multivariate Data Analysis for IBM PC Systems by Infometrix, Incorporated is an example of commercially available software which is useful for this purpose.

The preferred method for building the chemometric model includes the following steps: (1) entering as independent variables the second derivative absorption data from the sample data set taken from the production unit; (2) entering as dependent variables the thermogravimetric analysis of residue content of the samples; (3) excluding spectral data points which do not have a variance that can be related to the residue concentration, preferably including only data in the spectral region between 1715 nm and 1973 nm; (4) mean centering the data; and (5) performing a partial least squares regression analysis. The model is exported as a text file of coefficients to the control device (computer) used for spectrometer control and data analysis. The cross product sum of the coefficient file and any second derivative absorption spectrum file of the isocyanate residue mixture from the isocyanate production unit will generate the residue value. The spectral data from all the samples were converted to second derivative spectra and mean centered in order to eliminate baseline shifts between spectra and to provide a more robust model.

After the model has been completed and the analysis of samples has begun, it is possible to make adjustments in the isocyanate production and recovery processes in order to maximize isocyanate yield. For example, if analysis of the isocyanate/residue mixture determines that the residue content of the isocyanate/residue mixture is above 40%, the temperature in the isocyanate production vessel is reduced until the residue content is reduced to 25 to 30%.

In general, residue contents of from 25 to 35 percent are acceptable and do not require any adjustment. However, residue contents of greater than 40% indicate the need to adjust the isocyanate production and/or recovery process parameters such as temperature and/or pressure.

Having thus described our invention, the following Example is given as being illustrative thereof. All parts and percentages given in this Example are parts by weight or percentages by weight, unless otherwise indicated.

EXAMPLE

The method used to construct the residue content chemometric model and use of this model to determine the residue content of a mixture of isocyanate and residue from the isocyanate production process will be described using the residue formed during the production of toluene diisocyanate as an illustrative example. This particular isocyanate was chosen because the opaque and highly colored nature of the isocyanate/residue mixture and the variability in the composition of the residue were expected to challenge the capability of the monitoring technique.

In constructing the chemometric model, the residue content of each isoc,yanate/residue sample was determined in the laboratory by thermogravimetric analysis. Specifically, 20 to 80 milligrams of a sample of an isocyanate/residue mixture was placed in a 140 microliter alumina crucible. The crucible and sample were placed on a balance pan of a balance capable of measuring the weight of the sample to the nearest microgram. The balance pan was freely suspended in a tubular oven to avoid any interference with the function of the balance or determination of the weight of the sample. The oven used was capable of being programmed to increase its temperature from 20 to 600° C., preferably from 30 to 360° C., at a rate of from 0.1 to 50° C. per minute, preferably 10° C. per minute. The oven was also capable of being purged with a gas, preferably nitrogen, at 0 to 200 milliliters per minute, preferably 60 milliliters per minute. As the temperature in the oven was increased, the weight of the sample and the oven temperature were continuously recorded. From these data, a plot of weight versus temperature was constructed. This plot of weight versus temperature reflects the volatility behavior of the isocyanate and residue mixture. The residue content as a fraction of the sample may be defined as the weight of the sample remaining in the crucible at a specific temperature divided by the original weight of the sample placed in the crucible. The preferred temperature for determining the residue content in this Example was 280° C. The temperature chosen for the residue determination may vary from 100 to 400° C. depending on (1) the type of isocyanate and residue mixture for which a calibration is being made and (2) the volatility characteristics of the isocyanate and residue mixture.

A UOP Guided Wave Model 310 NIR Spectrometer was used to collect spectral data for a toluene diisocyanate/ residue mixture as it flowed through a pipeline of the toluene diisocyanate production unit. The light used to generate these spectra was emitted and gathered with a UOP Guided Wave Single Sided 1 cm Transmission Probe corresponding in structure to the probe illustrated in FIG. 1 which had been inserted into the pipeline. The probe was inserted into the pipeline in a manner such that the toluene diisocyanate/ residue mixture flowed through the probe sample cell. The probe was connected to the spectrometer as illustrated in FIG. 2 by means of UOP Guided Wave VIS-NIR Jacketed Optical Fiber part number P/N 12538-100 (available from UOP Guided Wave Process Analytical Systems of El Dorado Hills, Calif.) for the transmission of an NIR optical beam through the toluene diisocyanate/residue mixture contained within the sample cell of the probe. Raw spectral files generated by the spectrometer were transmitted to a Gateway 2000 Model 4DX2-66V computer over a RS-232 cable. The computer generated second derivative absorption spectral files of the samples previously analyzed for residue content by the thermogravimetric method. The spectral files and thermogravimetric results were combined and a multivariate regression analysis was performed using the statistical software program Pirouette Version 1.1 Multivariate Data Analysis for IBM PC Systems by Infometrix, Incorporated. Within the Pirouette program, the regression analysis was run with the following settings: (1) spectral data outside of the region of 1715 to 1973 nm were excluded; (2) the data were mean centered; and (3) a partial least squares regression analysis was performed. The calibration coefficients were exported as a text file. The coefficient data were used with second derivative absorption file data from the NIR spectrometer computer to generate a cross product sum equivalent to the residue content of the toluene diisocyanate/ residue mixture.

Figure 4:
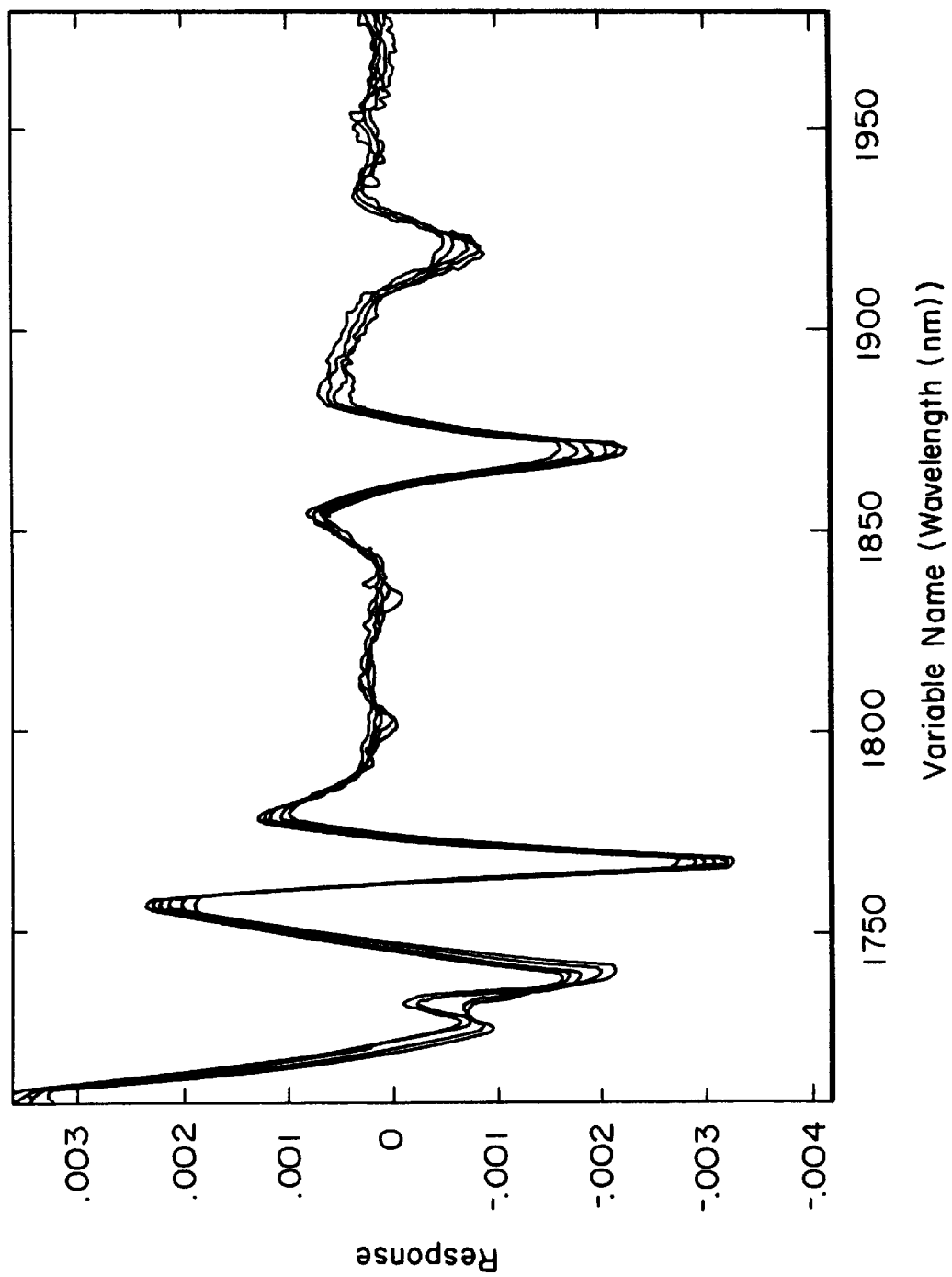
FIG. 4 is the 2nd derivative plot of the absorption spectra of FIG. 3 with the wavelength axis expanded to emphasize the active bands of the spectra.
Figure 5:
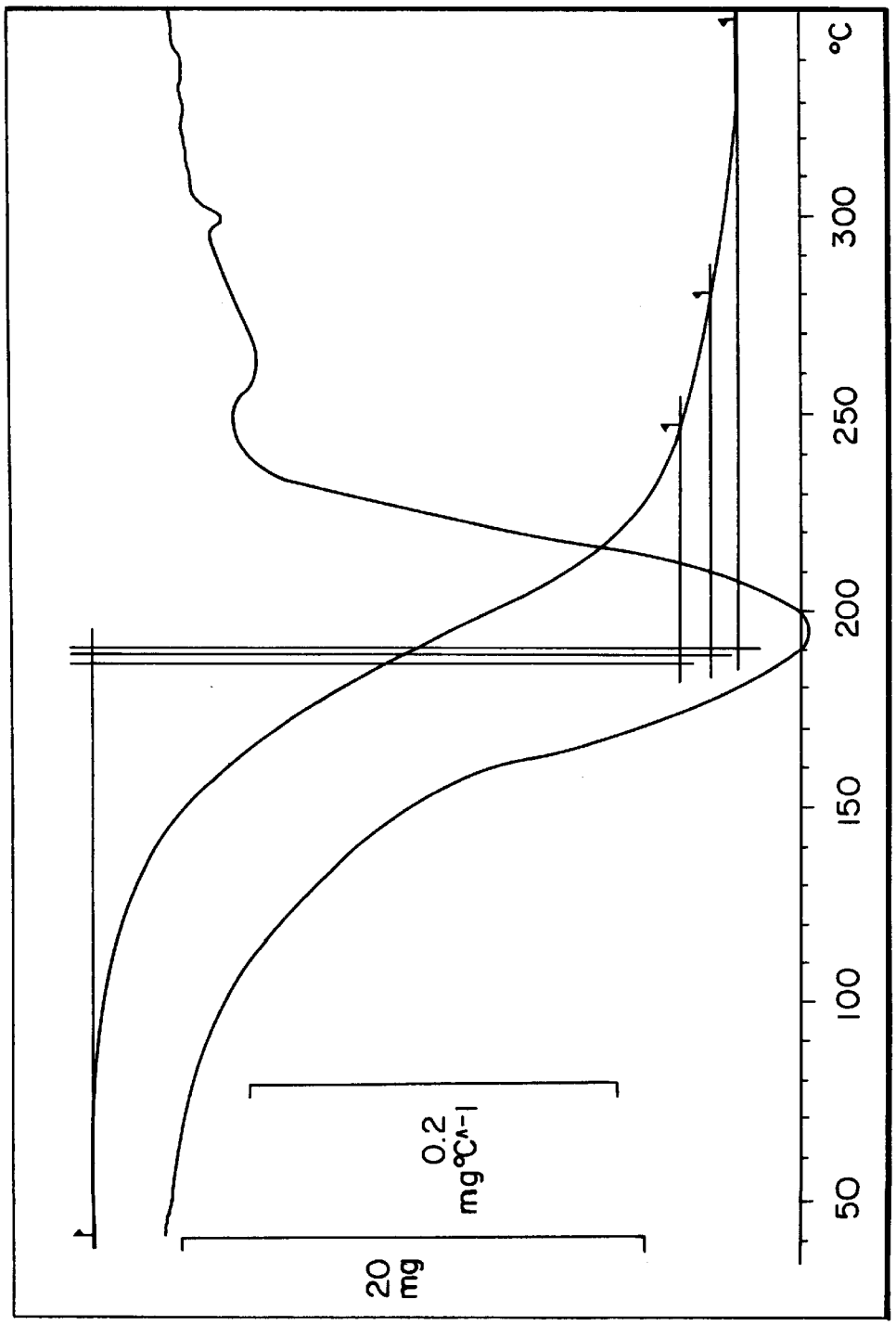
FIG. 5 is a plot of the thermogravimetric analysis (TGA) of one sample of a toluene diisocyanate/residue mixture.
Figure 6:
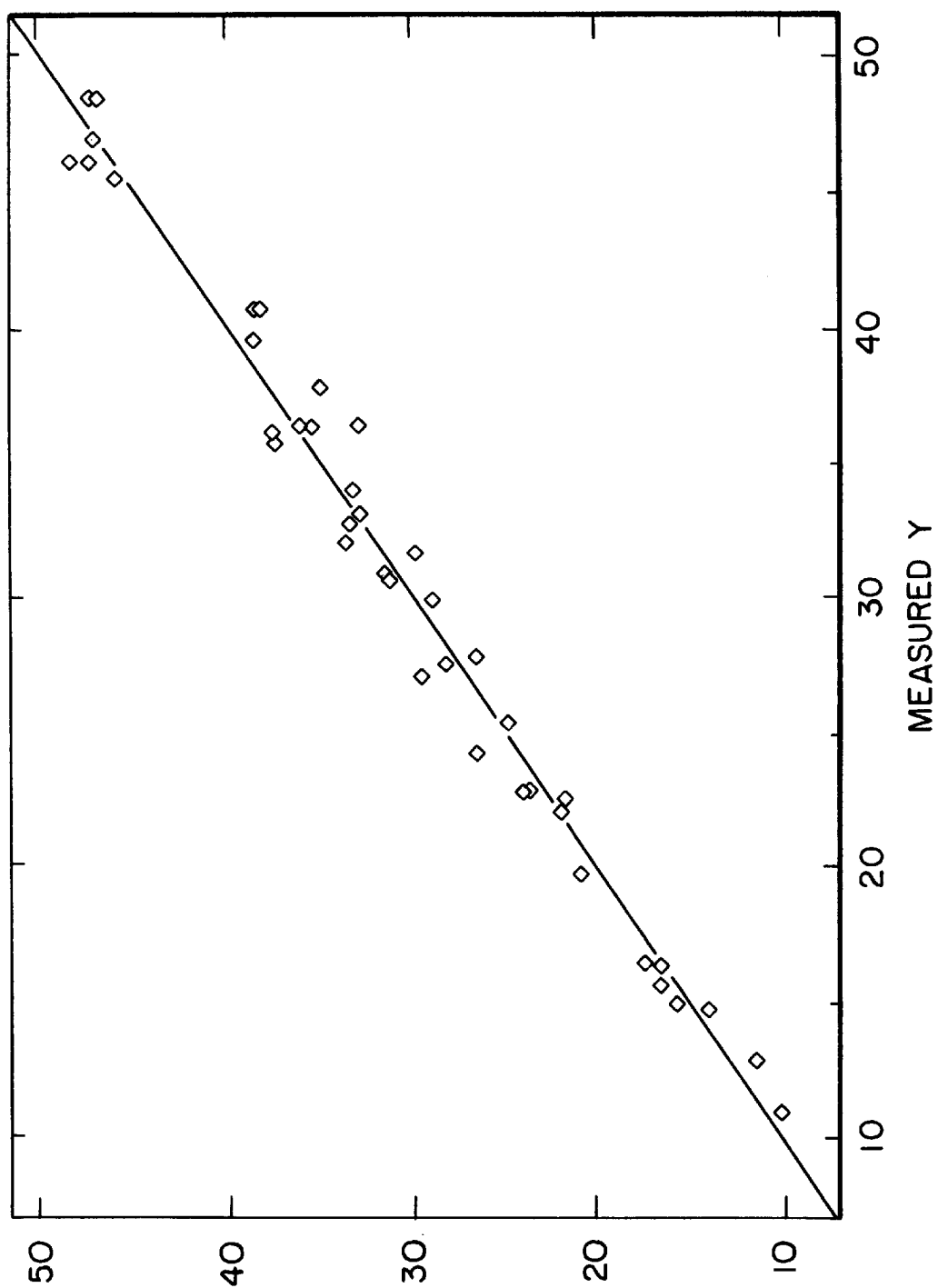
FIG. 6 is a multivariate regression plot of the second derivative spectrum shown in FIG. 4 correlated with the corresponding thermogravimetric analysis ("TGA" analysis) of the residue content shown in FIG. 5.

More specifically, 43 samples of toluene diisocyanate/ residue mixture were collected at a toluene diisocyanate production unit. Thermogravimetric analysis of these samples determined residue contents in the range of from 9 to 48% by weight. The results of spectral (plotted in FIG. 4) and thermogravimetric analysis (plotted in FIG. 5) were combined and a partial least squares regression calibration was performed (plotted in FIG. 6). An error of validation equal to 1.2% residue was obtained. The calibration coefficients were transferred to the computer controlling the NIR spectrometer and the residue content of the isocyanate residue mixture was output in real time as a 4–20 ma signal to the production process control computer.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An in-line spectrometric method for monitoring the residue content of an isocyanate/residue mixture with an accuracy of ±2% during an isocyanate production process comprising:

a) inserting into a stream of an isocyanate/residue mixture a probe capable of directing light at wavelengths of from 1050 to 2150 nanometers from a fiber optic cable through an isocyanate/residue mixture to another fiber optic cable which probe is connected to a near infrared spectrometer by said fiber optic cable, b) directing light at wavelengths of from 1050 to 2150 nanometers through the isocyanate/residue mixture with the probe inserted in a), c) collecting light absorption data generated during b), d) generating a second derivative near-infrared spectrum from the data collected in c), and e) determining the residue content of the isocyanate/residue mixture by means of a mathematical calibration model that correlates residue content with the spectrum generated in d).

2. The method of claim 1 in which absorbance information is collected from an isocyanate/residue mixture generated in a continuous isocyanate production process at regular, pre-determined time intervals during the isocyanate production process.

3. The method of claim 2 in which the absorbance information is gathered at intervals of from 1 to 15 minutes.

4. The method of claim 1 in which the probe used to gather the absorbance data is connected to a remote near infrared spectrometer.

5. The method of claim 4 in which the probe is connected to the remote near infrared spectrometer by fiber optic cables.

6. The method of claim 4 in which the remote near infrared spectrometer is connected to a computer which has been programmed to correlate the residue content with the absorbance spectrum generated by the infrared spectrometer.

7. The method of claim 1 in which the means for correlating absorbance information with residue content is a computer which is remote with respect to the probe that has been programmed to correlate residue content with absorbance information collected by the probe and near infrared spectrometer.

8. A method for monitoring an isocyanate production process comprising:

a) determining the residue content of isocyanate/residue mixtures generated during the isocyanate production process by the method of claim 1, and b) adjusting the temperature and/or pressure conditions of the isocyanate production process when the residue content determined in a) is greater than 20%.

9. An apparatus for in-line monitoring of residue content of an isocyanate/residue mixture with an accuracy of ±2% during an isocyanate production process comprising:

a) a probe capable of directing light at wavelengths of from 1050 to 2150 nanometers having a sample cell composed of
(1) two near infrared windows,
(2) an opening between the near infrared windows through which material to be analyzed may flow, b) a fiber optic cable which connects the probe a) to a near infrared light source, c) a near infrared light source connected to probe a) by fiber optic cable b)

d) a fiber optic cable which connects probe a) to a spectrometer, e) a spectrometer connected to probe a) by fiber optic cable d), and f) a means for analyzing data from spectrometer e) which is connected to spectrometer e).

10. The apparatus of claim 9 in which the data analyzing means f) is connected to a monitor g) on which data analysis may be displayed.

11. The apparatus of claim 9 in which the means for analyzing data f) also controls light emission from near infrared light source c) to probe a).

* * * * *